United States Patent
Ji et al.

(10) Patent No.: US 11,964,032 B2
(45) Date of Patent: Apr. 23, 2024

(54) AQUEOUS POLYURETHANE FUNCTIONAL MASK SUBSTRATE AND APPLICATION THEREOF

(71) Applicants: WANHUA CHEMICAL GROUP CO., LTD., Shandong (CN); WANHUA CHEMICAL (NINGBO) CO., LTD., Zhejiang (CN)

(72) Inventors: Xiaoxiao Ji, Shandong (CN); Haidong Jia, Shandong (CN); Nuo Xu, Shandong (CN); Shan Liu, Shandong (CN); Yunling Liu, Shandong (CN); Jie Zhang, Shandong (CN); Xueshun Ji, Shandong (CN); Jiakuan Sun, Shandong (CN)

(73) Assignees: WANHUA CHEMICAL GROUP CO., LTD., Shandong (CN); WANHUA CHEMICAL (NINGBO) CO., LTD., Zhejiang (CN)

( * ) Notice: Subject to any disclaimer, the term of this patent is extended or adjusted under 35 U.S.C. 154(b) by 481 days.

(21) Appl. No.: 17/278,533

(22) PCT Filed: Nov. 9, 2018

(86) PCT No.: PCT/CN2018/114894
§ 371 (c)(1),
(2) Date: Mar. 22, 2021

(87) PCT Pub. No.: WO2020/093393
PCT Pub. Date: May 14, 2020

(65) Prior Publication Data
US 2021/0353510 A1    Nov. 18, 2021

(30) Foreign Application Priority Data

Nov. 6, 2018    (CN) .......................... 201811311556.7

(51) Int. Cl.
| | | |
|---|---|---|
| *A61K 8/02* | (2006.01) | |
| *A61K 8/87* | (2006.01) | |
| *C08G 18/10* | (2006.01) | |
| *C08G 18/32* | (2006.01) | |
| *C08G 18/42* | (2006.01) | |
| *C08G 18/75* | (2006.01) | |
| *C08L 75/06* | (2006.01) | |

(52) U.S. Cl.
CPC .............. *A61K 8/0212* (2013.01); *A61K 8/87* (2013.01); *C08G 18/10* (2013.01); *C08G 18/3225* (2013.01); *C08G 18/4238* (2013.01); *C08G 18/758* (2013.01); *C08L 75/06* (2013.01); *A61K 2800/48* (2013.01); *A61K 2800/524* (2013.01); *A61K 2800/594* (2013.01)

(58) Field of Classification Search
CPC ................................ A61K 8/0212; A61K 8/87
See application file for complete search history.

(56) References Cited

U.S. PATENT DOCUMENTS

| | | | | |
|---|---|---|---|---|
| 2006/0079635 | A1* | 4/2006 | Pohl ........................ | C08J 9/30 524/589 |
| 2006/0084775 | A1* | 4/2006 | Rische .............. | C08G 18/0819 528/44 |
| 2006/0293468 | A1* | 12/2006 | Rische .............. | C08G 18/0828 525/457 |
| 2018/0303744 | A1* | 10/2018 | Dörr ....................... | A61Q 1/02 |

FOREIGN PATENT DOCUMENTS

| | | |
|---|---|---|
| CN | 101361701 A | 2/2009 |
| CN | 1943546 B | 5/2010 |
| CN | 102100651 A | 6/2011 |
| CN | 102793639 A | 11/2012 |
| CN | 104031225 A | 9/2014 |
| CN | 104042453 A | 9/2014 |
| CN | 104042502 A | 9/2014 |
| CN | 104352359 A | 2/2015 |
| CN | 104546549 A | 4/2015 |
| CN | 105012185 A | 11/2015 |
| CN | 206404053 U | 8/2017 |
| CN | 206548844 U | 10/2017 |
| CN | 108125795 A | 6/2018 |
| EP | 1174119 A1 | 1/2002 |
| KR | 101867210 B1 | 6/2018 |
| WO | 2020093393 A1 | 5/2020 |

OTHER PUBLICATIONS

International Search Report issued in PCT/CN2018/114894 on Feb. 20, 2019.
European Search Report issued Jul. 28, 2022 in corresponding patent application EP 18939481.1-1109.

* cited by examiner

Primary Examiner — Michael L Leonard
(74) Attorney, Agent, or Firm — Norton Rose Fulbright US LLP; James R. Crawford

(57) ABSTRACT

Disclosed by the present invention are an aqueous polyurethane functional mask substrate and an application thereof. Two kinds of water-based polyurethane dispersions are used as the main components of the mask substrate. The transdermal penetration and absorption of functional ingredients such as whitening, moisturizing and anti-aging ingredients in facial mask products are promoted by means of the special cross-linked structures of polyurethane films. During use, a mask is evenly applied to the face; and after the mask dries, the entire mask may be removed directly or removed after being moistened using water. The mask substrate according to the present invention is also applicable to body masks such as a hand mask, a neck mask and a back mask.

18 Claims, No Drawings

AQUEOUS POLYURETHANE FUNCTIONAL MASK SUBSTRATE AND APPLICATION THEREOF

This application is a national phase under 35 U.S.C. § 371 of International Application No. PCT/CN2018/114894 filed Nov. 9, 2018, which claims the benefit of priority from Chinese Application No. 201811311556.7 filed on Nov. 6, 2018. The entire contents of these applications are incorporated herein by reference in their entirety.

TECHNICAL FIELD

The present disclosure belongs to the field of chemical engineering, and relates to a mask substrate, specifically to an aqueous polyurethane functional mask substrate and an application thereof.

BACKGROUND

With the development of society and the improvement of people's quality of life, consumers have more requirements for cosmetics. Characteristics of facial mask products such as convenient use, obvious effects and instant moisturizing have gradually been widely recognized by consumers.

Currently, commercially available facial masks are mainly classified into non-woven masks, silk masks, bio-fiber masks, kaolin masks and powder blending masks according to their materials. Conventional facial masks mainly include carriers and skin care ingredients, and carriers mainly include non-woven fabrics, silks and the like. However, due to individual differences of human faces, conventional facial masks mainly have the following shortcomings during use: (1) the facial mask cannot fit the face completely; and (2) because of the skin barrier of the human body, especially the function of the stratum corneum, only a very small part of the active substances in the facial mask can be absorbed deeply through the epidermis.

In order to improve the shortcomings of conventional facial masks, superconductive masks and transdermal enhancers have been proposed as the main solutions. Chinese patent CN206404053 U discloses a superconductive haptogen alginate fiber facial mask cloth, and Chinese patent CN206548844 U discloses a superconductive facial mask of silver fiber. Both superconductive facial masks change the shape and material of the facial mask cloth to make the facial mask cloth better fit the face, which helps skin care ingredients to be introduced into the deep layers of skin. CN102793639 A, CN104042502 B, CN105012185 A and CN1943546 B respectively disclose several transdermal enhancers that can promote better absorption of active ingredients by the skin in cosmetics, and these transdermal enhancers are derived from natural plant extracts.

However, there is no report about using polyurethane polymer to form a functional mask substrate to promote the absorption of functional ingredients in the mask.

SUMMARY

The present disclosure provides an aqueous polyurethane functional mask substrate composition and an aqueous polyurethane functional mask substrate based on the mask substrate composition. The mask substrate composition or the mask substrate can promote the penetration and absorption of active substances, and the mask substrate can be conveniently and evenly applied on the face, so it fits perfectly on the face. Based on the mask substrate composition or the mask substrate of the present disclosure, facial or body mask products can be produced. When the products are in use, the mask substrate can effectively promote deep absorption of the active ingredients by the skin during the drying process, and meanwhile, the facial or body mask can be uncovered completely without pain.

In order to resolve the above problems, the present disclosure provides a mask substrate composition. The mask substrate composition includes the following components, by the total mass of the mask substrate composition:
  (a) 5-90 wt % of an aqueous polyurethane dispersion a, preferably 10-70 wt %, more preferably 10-50 wt %; and
  (b) 10-95 wt % of an aqueous polyurethane dispersion b, preferably 10-70 wt %, more preferably 10-50 wt %;
  where (a) the aqueous polyurethane dispersion a is prepared by reaction of reaction raw materials including (a2) polyester polyol, (a3) a low-molecular weight diol chain extender, (a1) polyisocyanate, (a4) a polyamine chain extender a, (a5) a polyamine chain extender b and (a6) a small-molecule monoamino end-capping agent;
  (a3) the low-molecular weight diol chain extender is a diol chain extender with a molecular weight of 80-120;
  (a4) the polyamine chain extender a is a polyamine chain extender which is not substituted by an ionic or potentially ionic group;
  (a5) the polyamine chain extender b is a polyamine chain extender which is substituted by an ionic or potentially ionic group; and
  (a6) the small-molecule monoamino end-capping agent is a monoamino end-capping agent with a molecular weight of 300 or less;
  (b) the aqueous polyurethane dispersion b is prepared by reaction of reaction raw materials including (b1) polyisocyanate, (b2) polyester polyol, (b3) polyethylene glycol monomethyl ether, (b6) a polyhydroxyl chain extender, (b4) a polyamine chain extender a' and (b5) a polyamine chain extender b';
  (b4) the polyamine chain extender a' is a polyamine chain extender which is not substituted by an ionic or potentially ionic group;
  (b5) the polyamine chain extender b' is a polyamine chain extender which is substituted by an ionic or potentially ionic group; and
  (b6) the polyhydroxyl chain extender is a low-molecular weight polyhydroxyl chain extender with a molecular weight of 300 or less.

In some preferred embodiments, in the above mask substrate composition, by the mass of polyurethane in (a) the aqueous polyurethane dispersion a, (a) the aqueous polyurethane dispersion a is prepared by reaction of reaction raw materials of the following mass percentages:
  (a2) polyester polyol 65-80 wt %, preferably 71-75 wt %;
  (a3) a low-molecular weight diol chain extender 0.1-3 wt %, preferably 0.5-1 wt %;
  (a1) polyisocyanate 15-25 wt %, preferably 19-23 wt %;
  (a4) a polyamine chain extender a 0.01-3 wt %, preferably 0.05-2 wt %;
  (a5) a polyamine chain extender b 1-8 wt %, preferably 2-5 wt %; and
  (a6) a small-molecule monoamino end-capping agent 0.1-2 wt %, preferably 0.4-1 wt %;
  preferably, (a) the aqueous polyurethane dispersion a is prepared according to a method including the following steps: mixing (a2) the polyester polyol and (a3) the low-molecular weight diol chain extender at 70-80° C., lowering the temperature of the resulting mixture to 45-60° C., and then adding (a1) the polyisocyanate for a prepolymerization reaction; cooling the resulting prepolymer to 30-45° C. when the theoretical NCO content is reached, and dissolving the prepolymer in an acetone solvent in which the usage amount of acetone is 100-150 wt % of the mass of the polyurethane in (a) the aqueous polyurethane dispersion a; after mixing the prepolymer and the acetone solvent, adding (a4) the polyamine chain extender a and (a5) the polyamine chain extender b, continuing the reaction at 35-45° C. for 15-30 min, adding water under shear and dispersion conditions in which the usage amount of water is 130-200 wt % of the mass of the polyurethane in (a) the aqueous polyurethane dispersion a, adding a diluted aqueous solution of (a6) the small-molecule monoamino end-capping agent for end-capping, removing the acetone under vacuum, and obtaining (a) the aqueous polyurethane dispersion a; and the total solids content of (a) the aqueous polyurethane dispersion a is 20-50 wt %, preferably 35-45 wt %; and the particle size is 100 nm-300 nm, preferably 150 nm-250 nm, such as 170 nm, 190 nm, 210 nm and 230 nm.

In any mask substrate composition described above, by the mass of polyurethane in (b) the aqueous polyurethane dispersion b, (b) the aqueous polyurethane dispersion b is prepared by reaction of reaction raw materials of the following mass percentages:

(b1) polyisocyanate 14-35 wt %, preferably 15-23 wt %;
(b2) polyester polyol 60-83.8 wt %, preferably 70-80 wt %;
(b3) polyethylene glycol monomethyl ether 1-3 wt %, preferably 1.8-2.5 wt %;
(b6) a polyhydroxyl chain extender 0.1-1 wt %, preferably 0.2-0.5 wt %;
(b4) a polyamine chain extender a' 0.1-5 wt %, preferably 0.5-2 wt %; and
(b5) a polyamine chain extender b' 1-2 wt %, preferably 1.4-1.6 wt %;

preferably, (b) the aqueous polyurethane dispersion b is prepared according to a method including the following steps:

mixing (b1) the polyisocyanate, (b2) the polyester polyol, (b3) the polyethylene glycol monomethyl ether, (b6) the polyhydroxyl chain extender and acetone at 50-100° C., performing a prepolymerization reaction, and dissolving the resulting prepolymer in an acetone solvent when the theoretical NCO content is reached or approached, in which the overall usage amount of acetone in the preparation process is 100-210 wt % of the mass of the polyurethane in (b) the aqueous polyurethane dispersion b; after mixing the prepolymer and the acetone solvent, adding (b4) the polyamine chain extender a' and (b5) the polyamine chain extender b', continuing the reaction at 35-45° C. for 15-30 min, adding water under shear and dispersion conditions in which the usage amount of water is 100-170 wt % of the mass of the polyurethane in (b) the aqueous polyurethane dispersion b, removing the acetone under vacuum, and obtaining (b) the aqueous polyurethane dispersion b; and the total solids content of (b) the aqueous polyurethane dispersion b is 30-50 wt %, and the particle size is 120 nm-190 nm, preferably 140 nm-160 nm.

In some preferred embodiments, in the above mask substrate composition, (a1) the polyisocyanate has two isocyanate groups, and is one or more selected from the group consisting of aliphatic isocyanates and alicyclic isocyanates, preferably one or more selected from the group consisting of isophorone diisocyanate, 1,6-hexyl diisocyanate, dicyclohexylmethane diisocyanate and tetramethyl xylylene diisocyanate, more preferably dicyclohexylmethane diisocyanate.

In some preferred embodiments, (a2) the polyester polyol has a number-average molecular weight of 800-3000, preferably 1000-2000, and a functionality of 2-3; and (a2) the polyester polyol is prepared by a polymerization reaction of organic polycarboxylic acid and/or anhydride thereof and polyol, where the organic polycarboxylic acid and/or anhydride thereof are one or more selected from the group consisting of succinic acid, glutaric acid, adipic acid, pimelic acid, suberic acid, azelaic acid, sebacic acid, phthalic acid, isophthalic acid, terephthalic acid and anhydrides thereof, preferably adipic acid; and the polyol includes one or more selected from the group consisting of ethylene glycol, 1,2-propylene glycol, 1,4-butylene glycol, 1,3-butylene glycol, 1,6-hexylene glycol, trimethylolpropane and neopentyl glycol, preferably 1,6-hexylene glycol and/or neopentyl glycol.

In some preferred embodiments, (a3) the low-molecular weight diol chain extender is one or more selected from the group consisting of ethylene glycol, diethylene glycol, 1,3-propylene glycol, 1,2-propylene glycol, 1,4-butylene glycol, 1,3-butylene glycol, cyclohexanediol, 1,4-cyclohexanedimethanol, 1,6-hexylene glycol and neopentyl glycol, preferably 1,4-butylene glycol and/or neopentyl glycol.

In some preferred embodiments, (a4) the polyamine chain extender a has 2-20 carbon atoms and a functionality of 2-3, and is preferably one or more selected from the group consisting of ethylenediamine, propylene diamine, butanediamine, hexamethylenediamine, isophorone diamine, 1,4-cyclohexanediamine, 4,4'-dicyclohexylmethanediamine and diethylenetriamine, more preferably one or more selected from the group consisting of ethylene diamine, hexamethylenediamine, isophorone diamine, 1,4-cyclohexanediamine and 4,4'-dicyclohexylmethanediamine, most preferably ethylene diamine and/or isophorone diamine.

In some preferred embodiments, (a5) the polyamine chain extender b is diamine substituted by an ionic or potentially ionic group, and is preferably a sodium salt of N-(2-aminoethyl)-2-aminoethanesulfonic acid and/or a sodium salt of N-(2-aminoethyl)-2-aminopropanesulfonic acid.

In some preferred embodiments, (a6) the small-molecule monoamino end-capping agent has 2-10 carbon atoms and a functionality of 1, and is preferably diethanol amine, trihydroxy amine and/or 2-amino-2-methyl-1-propanol, more preferably 2-amino-2-methyl-1-propanol.

In some preferred embodiments, in the above mask substrate composition, (b1) the polyisocyanate has 2-4 isocyanate groups, and is one or more selected from the group consisting of aliphatic polyisocyanates and alicyclic polyisocyanates, preferably one or more selected from the group consisting of hexamethylene diisocyanate, dodecamethylene diisocyanate, isophorone diisocyanate, and 4,4'-dicyclohexylmethane diisocyanate, more preferably 4,4'-dicyclohexylmethane diisocyanate.

In some preferred embodiments, (b2) the polyester polyol has a number-average molecular weight of 20-14000, preferably 500-3000, and a functionality of 2-3; and (b2) the polyester polyol is prepared by a polymerization reaction of organic polycarboxylic acid and/or anhydride thereof and polyol, where the organic polycarboxylic acid and/or anhydride thereof are one or more selected from the group consisting of succinic acid, adipic acid, suberic acid, isophthalic acid and anhydrides thereof, preferably isophthalic acid and/or adipic acid; and the polyol includes one or more selected from the group consisting of ethylene glycol, butanediol, neopentyl glycol and hexylene glycol, preferably butanediol and/or neopentyl glycol.

In some preferred embodiments, the number-average molecular weight of (b3) the polyethylene glycol monomethyl ether is 700-2000, preferably 1000-1500.

In some preferred embodiments, (b4) the polyamine chain extender a' has 2-13 carbon atoms and a functionality of 2-3, and is preferably one or more selected from the group consisting of 1,2-ethylenediamine, 1,6-hexamethylenediamine, 1-amino-3,3,5-trimethyl-5-aminomethyl-cyclohexane (isophorone diamine), piperazine, 1,4-diaminocyclohexane, bis-(4-aminocyclohexyl)methane, N-(2-hydroxyethyl)ethylenediamine and diethylene triamine, more preferably one or more selected from the group consisting of 1,6-hexamethylenediamine, 1-amino-3,3,5-trimethyl-5-aminomethyl-cyclohexane (isophorone diamine) and N-(2-hydroxyethyl)ethylenediamine, most preferably 1-amino-3,3,5-trimethyl-5-aminomethyl-cyclohexane (isophorone diamine) and/or 1,6-hexamethylenediamine.

In some preferred embodiments, (b5) the polyamine chain extender b' is diamine substituted by an ionic or potentially ionic group, and is preferably a sodium salt of N-(2-aminoethyl)-2-aminoethanesulfonic acid and/or a sodium salt of N-(2-aminoethyl)-2-aminopropanesulfonic acid.

In some preferred embodiments, (b6) the polyhydroxyl chain extender is trimethylolpropane.

In order to resolve the above problems, the present disclosure further provides a mask substrate. The mask substrate includes any mask substrate composition described above. By the total mass of the mask substrate, the mass percentages of (a) the aqueous polyurethane dispersion a and (b) the aqueous polyurethane dispersion b in the mask substrate composition in the mask substrate are as follows:
- (a) 5-90 wt % of the aqueous polyurethane dispersion a, preferably 10-70 wt %, more preferably 10-50 wt %; and
- (b) 10-95 wt % of the aqueous polyurethane dispersion b, preferably 10-70 wt %, more preferably 10-50 wt %;

preferably, by the total mass of the mask substrate, the mask substrate further includes components of the following mass percentages:
- (c) 0-10 wt % of a thickener, preferably 0.05-8 wt %, more preferably 0.1-6 wt %;
- (d) 0-10 wt % of an emulsifier, preferably 0.5-8 wt %, more preferably 1-7 wt %;
- (e) 0-20 wt % of a grease, preferably 2-18 wt %, more preferably 3-15 wt %;
- (f) 0-1 wt % of a preservative;
- (g) 0-3 wt % of a fragrance; and
- (h) 0-80 wt % of deionized water;
- where (d) the emulsifier can increase the stability of the grease, oil-soluble active ingredients, oil-soluble fragrances and preservatives in the mask; and
- (e) the grease can improve the skin feel of the functional mask substrate and increase the dissolution of oil-soluble active substances.

In the above mask substrate, the mask substrate is in an emulsion form, and by the total mass of the mask substrate, includes the following components:
- (a) 20-70 wt % of the aqueous polyurethane dispersion a;
- (b) 20-70 wt % of the aqueous polyurethane dispersion b;
- (c) 0-5 wt % of a thickener, preferably 0.05-3.5 wt %, more preferably 0.15-2.5 wt %;
- (d) 0-6 wt % of an emulsifier, preferably 0.5-5 wt %, more preferably 1-4 wt %;
- (e) 0-10 wt % of a grease, preferably 2-8 wt %, more preferably 3-6 wt %;
- (f) 0-1 wt % of a preservative;
- (g) 0-3 wt % of a fragrance; and
- (h) 0-60 wt % of deionized water.

In the above mask substrate, the mask substrate is in a cream form, and by the total mass of the mask substrate, includes the following components:
- (a) 10-50 wt % of the aqueous polyurethane dispersion a;
- (b) 10-50 wt % of the aqueous polyurethane dispersion b;
- (c) 0.2-10 wt % of a thickener, preferably 0.5-8 wt %, more preferably 1-6 wt %;
- (d) 0-7 wt % of an emulsifier, preferably 0.5-6 wt %, more preferably 1-5 wt %;
- (e) 0-15 wt % of a grease, preferably 2-13 wt %, more preferably 4-10 wt %;
- (f) 0-1 wt % of a preservative;
- (g) 0-3 wt % of a fragrance; and
- (h) 0-79.8 wt % of deionized water.

In the above mask substrate, the mask substrate is in a gel form, and by the total mass of the mask substrate, includes the following components:
- (a) 10-60 wt % of the aqueous polyurethane dispersion a;
- (b) 10-60 wt % of the aqueous polyurethane dispersion b;
- (c) 0.5-10 wt % of a thickener, preferably 1-8 wt %, more preferably 1.5-5 wt %;
- (d) 0-10 wt % of an emulsifier, preferably 1-8 wt %, more preferably 3-7 wt %;
- (e) 0-20 wt % of a grease, preferably 3-18 wt %, more preferably 5-15 wt %;
- (f) 0-1 wt % of a preservative;
- (g) 0-3 wt % of a fragrance; and
- (h) 0-71.5 wt % of deionized water.

In some preferred embodiments, in any mask substrate described above, (c) the thickener is one or more selected from the group consisting of acrylic thickener, polyurethane thickener (HEUR), cellulosic thickener, gellan gum, xanthan gum, carbomer, guar gum, diatomaceous earth, starch, arabic gum, soy protein gum, gelatin, sodium alginate, casein, chitosan, natural lanolin and agar.

In some preferred embodiments, (d) the emulsifier is one or more selected from the group consisting of stearyl esters, polyether silicone oils, alkyl ethers, carboxylates, sulfates, sulfonates, amine derivatives, polyoxyethylene ethers and polyoxypropylene ethers.

In some preferred embodiments, (e) the grease is one or more selected from the group consisting of natural oil, synthetic oil, mineral oil, fatty acid, fatty alcohol and fatty ester, preferably one or more selected from the group consisting of calendula oil, olive oil, lanolin oil, castor oil, cottonseed oil, soybean oil, sesame oil, almond oil, peanut oil, corn oil, rice bran oil, tea seed oil, sea buckthorn oil, avocado oil, Kukui oil, European nut oil, walnut oil, cocoa oil, mink oil, egg yolk oil, coconut oil, lecithin, squalane, lanolin derivatives, polysiloxane, fatty acid, fatty alcohol, fatty acid ester, glycerin and petrolatum.

In some preferred embodiments, (f) the preservative is a preservative mild to the skin, and is preferably one or more selected from the group consisting of phenoxy ethanol, ethylhexylglycerin, caprylyl glycol and 1,2-hexylene glycol.

In some preferred embodiments, in the above mask substrate in the emulsion form, by the total mass of the mask substrate, (c) the thickener is: 0-3.0 wt % of hydroxyethyl cellulose, 0-3.0 wt % of xanthan gum and 0-2.0 wt % of carbomer, preferably 0.05-1 wt % of hydroxyethyl cellulose, 0.05-1.0 wt % of xanthan gum and 0.05-0.5 wt % of carbomer to achieve better appearance and skin feel experience;
  (d) the emulsifier is 0-4.0 wt % of ceteareth-20 and 0-4.0 wt % of PEG-10 polydimethylsiloxane, preferably 2-3.0 wt % of ceteareth-20 and 2-3.0 wt % of PEG-10 polydimethylsiloxane to achieve better appearance and skin feel experience;
  (e) the grease is 0-10 wt % of coconut oil, 0-10 wt % of castor oil and 0-10 wt % of polydimethylsiloxane, preferably 2.0-10 wt % of coconut oil, 2.0-10 wt % of castor oil and 2.0-10 wt % of polydimethylsiloxane to achieve better appearance and skin feel experience.

In some preferred embodiments, in the above mask substrate in the cream form, by the total mass of the mask substrate, (c) the thickener is: 0.1-5.0 wt % of hydroxyethyl cellulose, 0.1-5.0 wt % of xanthan gum and 0-5.0 wt % of carbomer, preferably 0.5-3.0 wt % of hydroxyethyl cellulose, 0.5-3 wt % of xanthan gum and 0.8-3.0 wt % of carbomer to achieve better appearance and skin feel experience;
  (d) the emulsifier is 0-4.0 wt % of ceteareth-20 and 0-5.0 wt % of PEG-10 polydimethylsiloxane, preferably 1.0-4.0 wt % of ceteareth-20 and 1.0-5.0 wt % of PEG-10 polydimethylsiloxane to achieve better appearance and skin feel experience;
  (e) the grease is 2.0-10 wt % of coconut oil, 2.0-10 wt % of castor oil and 2.0-10 wt % polydimethylsiloxane, preferably 5.0-10 wt % of coconut oil, 4.0-10 wt % of castor oil and 5.0-10 wt % of polydimethylsiloxane to achieve better appearance and skin feel experience.

In some preferred embodiments, in the above mask substrate in the gel form, by the total mass of the mask substrate, (c) the thickener is: 0.1-2.0 wt % of gellan gum, 0.1-6.0 wt % of xanthan gum and 0.1-5.0 wt % of carbomer, preferably 0.1-1.5 wt % of gellan gum, 1.0-1.5 wt % of xanthan gum and 1.0-4.0 wt % of carbomer to achieve better appearance and skin feel experience;
  (d) the emulsifier is 0-4.0 wt % of ceteareth-20 and 0-4.5 wt % of PEG-10 polydimethylsiloxane, preferably 1.0-3.0 wt % of ceteareth-20 and 1.0-4.5 wt % of PEG-10 polydimethylsiloxane to achieve better appearance and skin feel experience;
  (e) the grease is 0-10 wt % of coconut oil, 0-12 wt % of castor oil and 0-12 wt % of polydimethylsiloxane, preferably 4-10 wt % of coconut oil, 3-10 wt % of castor oil and 4-12 wt % of polydimethylsiloxane to achieve better appearance and skin feel experience.

In order to resolve the above problems, the present disclosure further provides a method for preparing any mask substrate described above. The method includes the following steps:
  (a) the aqueous polyurethane dispersion a and (b) the aqueous polyurethane dispersion b are mixed to obtain a phase A; (h) the deionized water and (c) the thickener are mixed to obtain a phase B; and (d) the emulsifier and (e) the grease are mixed to obtain a phase C;
  in the presence of the phase C, the phase B and the phase C are respectively heated to 70-85° C. and mixed well to obtain a phase B+C, and after the temperature drops to the range of 50° C. to room temperature, the phase A and other components are added and mixed well; and
  in the absence of the phase C, the phase A and the phase B are mixed at the room temperature to obtain a phase A+B, and other components are added and mixed well.

The other components include (f) the preservative and/or (g) the fragrance.

In order to resolve the above problems, the present disclosure further provides a facial mask or body mask. The facial mask or body mask includes any mask substrate composition described above or any mask substrate described above and an active substance.

The body mask is preferably a neck mask, a back mask or a leg mask.

The active substance includes, but is not limited to, active ingredients such as whitening, freckle removal, anti-oxidation, moisturizing and/or anti-wrinkle ingredients.

In order to resolve the above problems, the present disclosure further provides a method for preparing the facial mask or body mask. The method includes a step of mixing any mask substrate composition described above or any mask substrate described above and the active substance.

In order to resolve the above problems, the present disclosure further provides an application of any mask substrate composition described above or any mask substrate described above or the facial mask or body mask described above in the promotion of penetration and absorption of active substances, preferably an application in the promotion of penetration and absorption of active substances in skin.

In the present disclosure, for the first time, by means of an aqueous polyurethane mask substrate having the function of promoting the penetration and absorption of active substances, the functional ingredients in the cosmetics can pass through the skin barrier to be better absorbed by the skin. The aqueous polyurethane mask substrate of the present disclosure has at least the following two beneficial effects.

1. According to different demands of users, the aqueous polyurethane mask substrate of the present disclosure can be partially or completely applied to the face. When the mask dries, it can be completely attached to the face. The mask can be uncovered directly or after being wetted with water without any pain. In the uncovering process, the mask will not stick to the skin and tear the pores, so it will not cause any problems of loose skin and enlarged pores. On the contrary, the mask has the effect of shrinking pores and tightening the skin during the drying process, leaving the skin in a more perfect state.
2. The aqueous polyurethane mask substrate of the present disclosure has good compatibility with various active ingredients of cosmetics, such as whitening, moisturizing and anti-wrinkle ingredients. In the film forming process, two aqueous polyurethanes having special cross-linked structures interact with each other to achieve the effect of leading the active ingredients deep into the skin. In this way, the active ingredients are better absorbed by the human body, so that the functional mask products can achieve better effects. However, the use of one of the aqueous polyurethanes alone does not significantly promote the absorption of the active ingredients.

DETAILED DESCRIPTION

Experimental methods applied in the following examples are conventional methods without otherwise specified.

All the materials and reagents applied in the following examples are commercially available without otherwise specified.

The present disclosure will be further described hereinafter with reference to the specific examples. It is to be understood that the examples described below are provided to illustrate the present disclosure and should not be construed as limiting the scope of the present disclosure.

CMA-654 (polyneopentanediol adipate-hexanediol diol with a number-average molecular weight of about 1500 and an OH value of 74 mg KOH/g) is a product available from HuaDa Chemical Group Co., Ltd (Yantai).

WANNATE®HMDI (4.4'-dicyclohexylmethane diisocyanate) is a product available from Wanhua Chemical Group Co., Ltd.

VESTAMIN®A95 (sodium N-(2-aminoethyl)-2-aminoethanesulphonate) is a product available from Evonik Industries.

AMP-95 (2-amino-2-methyl-1-propanol with a molecular weight of 89.14) is a product available from Dow Chemical Company.

Isophorone diamine is a product available from Bayer.

PBA2000 (poly(1,4-butylene glycol adipate) diol with a number-average molecular weight of 2000, a functionality of 2 and an OH value of 56 mg KOH/g) is a product available from HuaDa Chemical Group Co., Ltd (Yantai).

PN110 (polyneopentanediol terephthalate diol with a number-average molecular weight of 1000 and a functionality of 2) is a product available from Stepan (Nanjing) Chemical Co., Ltd.

MPEG1200 (polyethylene glycol monomethyl ether with a number-average molecular weight of 1200) is a product available from LOTTE Chemical Co., Ltd., South Korean.

TMP (trimethylolpropane) is a product available from Fufeng Perstorp Chemical Co., Ltd, Shandong.

The anionic aqueous polyurethane dispersion—1a was synthesized according to the following method: 250 g of CMA-654 (71.18 wt %, where wt % represented a mass percentage relative to the solid (i.e., polyurethane) in the anionic aqueous polyurethane dispersion—1a, the same below) and 1.8 g of neopentyl glycol (0.51 wt %) were added to a four-necked flask, mixed and stirred for 10 min at 70° C. and then cooled to 50° C.; 78 g of WANNATE®HDI (22.21 wt %) was added to perform a prepolymerization reaction; the reaction was tested, and when NCO %=2.66 wt %, the resulting prepolymer was cooled to 40° C. and dissolved in 360 g of acetone solvent (102.5 wt %); the prepolymer and the acetone solvent were mixed for 15 min, and a solution formed by 3.2 g of ethylenediamine (0.91 wt %), 15.7 g of VESTAMIN®A95 (4.46 wt %) and 75.6 g of deionized water was added; the reaction was continued for 30 min at 45° C., then 575 g of water (163.2 wt %) was added under shear and dispersion conditions, and a diluted aqueous solution of 2.5 g of AMP-95 (0.71 wt %) was added to end-cap the resulting emulsion; the acetone was removed by distillation at reduced pressure to obtain a polyurethane dispersion with a solids content of about 40 wt % and a particle size of 240 nm, i.e., the anionic aqueous polyurethane dispersion—1a.

The anionic aqueous polyurethane dispersion—2a was synthesized according to the following method: 250 g of CMA-654 (75.02 wt %, where wt % represented a mass percentage relative to the solid (i.e., polyurethane) in the anionic aqueous polyurethane dispersion—2a, the same below) and 2.5 g of 1,4-butylene glycol (0.75 wt %) were added to a four-necked flask, mixed and stirred for 10 min at 70° C. and then cooled to 50° C.; 65 g of WANNATE®HMDI (19.50 wt %) was added to perform a prepolymerization reaction; the reaction was tested, and when NCO %=1.30 wt %, the resulting prepolymer was cooled to 40° C. and dissolved in 330 g of acetone solvent (99.0 wt %); the prepolymer and the acetone solvent were mixed for 15 min, and a solution formed by 0.2 g of ethylenediamine (0.06 wt %), 14 g of VESTAMIN®A95 (4.20 wt %) and 56.8 g of deionized water was added; the reaction was continued for 30 min at 45° C., then 498 g of water (149.54 wt %) was added under shear and dispersion conditions, and a diluted aqueous solution of 1.5 g of AMP-95 (0.45 wt %) was added to end-cap the resulting emulsion; the acetone was removed by distillation at reduced pressure to obtain a polyurethane dispersion with a solids content of about 40 wt % and a particle size of 230 nm, i.e., the anionic aqueous polyurethane dispersion—2a.

The anionic aqueous polyurethane dispersion—3a was synthesized according to the following method: 250 g of CMA-654 (71.2 wt %, where wt % represented a mass percentage relative to the solid (i.e., polyurethane) in the anionic aqueous polyurethane dispersion—3a, the same below) and 3 g of neopentyl glycol (0.86 wt %) were added to a four-necked flask, mixed and stirred for 10 min at 70° C. and then cooled to 50° C.; 75 g of WANNATE®HMDI (21.38 wt %) was added to perform a prepolymerization reaction; the reaction was tested, and when NCO %=2.13 wt %, the resulting prepolymer was cooled to 40° C. and dissolved in 350 g of acetone solvent (100 wt %); the prepolymer and the acetone solvent were mixed for 15 min, and a solution formed by 5 g of isophorone diamine (1.42 wt %), 15.5 g of VESTAMIN®A95 (4.42 wt %) and 82 g of deionized water was added; the reaction was continued for 30 min at 45° C., then 520 g of water (148.5 wt %) was added under shear and dispersion conditions, and a diluted aqueous solution of 2.3 g of AMP-95 (0.66 wt %) was added to end-cap the resulting emulsion; the acetone was removed by distillation at reduced pressure to obtain a polyurethane dispersion with a solids content of about 40 wt % and a particle size of 210 nm, i.e., the anionic aqueous polyurethane dispersion—3a.

The anionic aqueous polyurethane dispersion—1b was synthesized according to the following method: 65 g of WANNATE®HMDI (18.40 wt %, where wt % represented a mass percentage relative to the solid (i.e., polyurethane) in the anionic aqueous polyurethane dispersion—1b, the same below), 225 g of PBA2000 (63.39 wt %), 50 g of PN110 (14.15 wt %), 5 g of MPEG1200 (1.42 wt %), 1 g of TMP (0.28 wt %) and 30 g of acetone were added to a four-necked flask and stirred well at 70° C., and a prepolymerization reaction was performed for 2-3 h; the reaction was tested for NCO, and when NCO %=1.55 wt %, the prepolymer was dissolved in 500 g of acetone (the total usage amount of acetone in the preparation process was 140 wt %); the prepolymer and the acetone were mixed for 15 min, and a solution formed by 3.8 g of hexamethylenediamine (1.08 wt %), 4.5 g of VESTAMIN®A95 (1.27 wt %) and 20 g of deionized water was added; the reaction was continued for 30 min at 45° C., then 421 g of water (117.88 wt %) was added under shear and dispersion conditions; the acetone was removed by distillation at reduced pressure to obtain a polyurethane dispersion with a solids content of about 47 wt % and a particle size of 150 nm, i.e., the anionic aqueous polyurethane dispersion—1b.

The anionic aqueous polyurethane dispersion—2b was synthesized according to the following method: 75 g of WANNATE®HMDI (30.36 wt %, where wt % represented a mass percentage relative to the solid (i.e., polyurethane) in the anionic aqueous polyurethane dispersion—2b, the same below), 150 g of PN110 (60.73 wt %), 6.5 g of MPEG1200 (2.63 wt %), 2 g of TMP (0.81 wt %) and 30 g of acetone were added to a four-necked flask and stirred well at 70° C., and a prepolymerization reaction was performed for 2-3 h; the reaction was tested for NCO, and when NCO %=3.1 wt %, the prepolymer was dissolved in 500 g of acetone (the total usage amount of acetone in the preparation process was 202.5 wt %); the prepolymer and the acetone were mixed for 15 min, and a solution formed by 10 g of hexamethylenediamine (4.05 wt %), 4.5 g of VESTAMIN®A95 (1.82 wt %) and 20 g of deionized water was added; the reaction was continued for 30 min at 45° C., then 403 g of water (163.22 wt %) was added under shear and dispersion conditions; the acetone was removed by distillation at reduced pressure to obtain a polyurethane dispersion with a solids content of about 47 wt % and a particle size of 140 nm, i.e., the anionic aqueous polyurethane dispersion—2b.

The anionic aqueous polyurethane dispersion—3b was synthesized according to the following method: 40 g of WANNATE®HMDI (14.84 wt %, where wt % represented a mass percentage relative to the solid (i.e., polyurethane) in the anionic aqueous polyurethane dispersion—3b, the same below), 220 g of PBA2000 (81.48 wt %), 5 g of MPEG1200 (1.85 wt %), 1 g of TMP (0.37 wt %) and 30 g of acetone were added to a four-necked flask and stirred well at 70° C., and a prepolymerization reaction was performed for 2-3 h; the reaction was tested for NCO, and when NCO %=1.15 wt %, the prepolymer was dissolved in 500 g of acetone (the total usage amount of acetone in the preparation process was 185 wt %); the prepolymer and the acetone were mixed for 15 min, and a solution formed by 0.5 g of hexamethylenediamine (0.19 wt %), 4.5 g of VESTAMIN®A95 (1.66 wt %) and 20 g of deionized water was added; the reaction was continued for 30 min at 45° C., then 415 g of water (153.55 wt %) was added under shear and dispersion conditions; the acetone was removed by distillation at reduced pressure to obtain a polyurethane dispersion with a solids content of about 47 wt % and a particle size of 160 nm, i.e., the anionic aqueous polyurethane dispersion—3b.

Hydroxyethyl cellulose is a product available from Dow Chemical Company (catalog No.: CELLOSIZE™ HYDROXYETHYL CELLULOSE QP100MH), and is a thickener.

Xanthan gum is a product available from Jungbunzlauer Company (catalog No.: E415food grade), and is a thickener.

Carbomer is a product available from Lubrizol (catalog No.: Carbopol®Ultrez 21), and is a thickener.

Gellan gum is a product available from CPKelco (catalog No.: KELCOGEL®Xanthan Gum), and is a thickener.

Ceteareth-20 is a product available from Cognis (catalog No.: EUMULGIN B2), and is an emulsifier.

PEG-10 polydimethylsiloxane is a product available from Guangdong BioMax Si&F New Material Co., Ltd. (catalog No.: BioMaxSF-9336), and is an emulsifier.

Coconut oil is a product available from Guangzhou Hanbaisi Daily Chemical Technology Development Co., Ltd., and is a grease.

Castor oil is a product available from Jinan Xinnuo Chemical Industry Co., Ltd., and is a grease.

Polydimethylsiloxane is a product available from Dow Corning (catalog No.: DC200-350 B2), and is a grease.

Fragrance is a product available from Shanghai FU-SHI Flavors & Fragrances Co., Ltd. (catalog No.: OLY007 BOOMBASTIC).

Phenoxy ethanol is a product available from Dow Chemical Company (catalog No.: NEOLONE™ PH100), and is a preservative.

Hydrolyzed glycosaminoglycan is a product available from Guangzhou Futureway Biotechnology Co., Ltd. (catalog No.: d-Factor®PLUS), and is a humectant.

The numerical values shown in the tables of the following examples and comparative examples are mass percentages, which specifically represent the percentages of the masses of each component to the sum of the masses of each component of the mask substrate.

Examples 1-13

According to the components and their mass percentages shown in Table 1, in the presence of the phase C (Examples 3, 5, 6, 8, 9, 10, 11, 12 and 13), the components of the phase B and the components of the phase C were mixed at room temperature, stirred at 600 r/min for 5 min and then heated to 75° C. respectively, and the phase B and the phase C were mixed and homogenized at 8000 r/min for 5 min during which the temperature was maintained at 75° C. to obtain a phase B+C. After the temperature dropped to 50° C., the phase A and other components were added and homogenized at 5000 r/min for 5 min to prepare the mask substrate. In the absence of the phase C (Examples 1, 2, 4 and 7), the components of the phase A and the components of the phase B were mixed at room temperature respectively, the phase A and the phase B were mixed to obtain a phase A+B, and other components (if any) were added to the phase A+B and homogenized at 5000 r/min for 5 min to prepare the mask substrate.

TABLE 1

| | Components | Example 1 | Example 2 | Example 3 | Example 4 | Example 5 | Example 6 | Example 7 |
|---|---|---|---|---|---|---|---|---|
| Phase A | Anionic aqueous polyurethane dispersion - 1a | 20 | 0 | 0 | 10 | 0 | 0 | 10 |
| | Anionic aqueous polyurethane dispersion - 2a | 0 | 70 | 0 | 0 | 50 | 0 | 0 |
| | Anionic aqueous polyurethane dispersion - 3a | 0 | 0 | 20 | 0 | 0 | 19 | 0 |

TABLE 1-continued

|  | Components | | | | | | | |
|---|---|---|---|---|---|---|---|---|
|  | Anionic aqueous polyurethane dispersion - 1b | 70 | 0 | 0 | 50 | 0 | 0 | 10 |
|  | Anionic aqueous polyurethane dispersion - 2b | 0 | 20 | 20 | 0 | 10 | 0 | 0 |
|  | Anionic aqueous polyurethane dispersion - 3b | 0 | 0 | 0 | 0 | 0 | 11 | 0 |
| Phase B | Water | 10 | 10 | 35 | 29.7 | 11.8 | 54.4 | 70 |
|  | hydroxyethyl cellulose | 0 | 0 | 3 | 5 | 0.1 | 0 | 0 |
|  | xanthan gum | 0 | 0 | 2 | 5 | 0.1 | 1 | 6 |
|  | Carbomer | 0 | 0 | 0 | 0 | 5 | 2 | 2 |
|  | Gellan gum | 0 | 0 | 0 | 0 | 0 | 0 | 2 |
|  | Ceteareth-20 | 0 | 0 | 3 | 0 | 4 | 2 | 0 |
| Phase C | PEG-10 Polydimethylsiloxane | 0 | 0 | 3 | 0 | 2 | 1 | 0 |
|  | Coconut oil | 0 | 0 | 3 | 0 | 5 | 3 | 0 |
|  | Castor oil | 0 | 0 | 3 | 0 | 3 | 3 | 0 |
|  | Polydimethylsiloxane | 0 | 0 | 4 | 0 | 5 | 3 | 0 |
| Other components | Fragrance | 0 | 0 | 3 | 0 | 0 | 0.3 | 0 |
|  | Phenoxyethanol | 0 | 0 | 1 | 0.3 | 1 | 0.3 | 0 |
| Substrate type |  | Emulsion | Emulsion | Emulsion | Cream | Cream | Cream | Gel |

|  | Components | Example 8 | Example 9 | Example 10 | Example 11 | Example 12 | Example 13 |
|---|---|---|---|---|---|---|---|
| Phase A | Anionic aqueous polyurethane dispersion - 1a | 0 | 0 | 10 | 30 | 12 | 11 |
|  | Anionic aqueous polyurethane dispersion - 2a | 10 | 0 | 0 | 0 | 0 | 0 |
|  | Anionic aqueous polyurethane dispersion - 3a | 0 | 30 | 0 | 0 | 0 | 0 |
|  | Anionic aqueous polyurethane dispersion - 1b | 0 | 0 | 0 | 35 | 22 | 20 |
|  | Anionic aqueous polyurethane dispersion - 2b | 60 | 0 | 35 | 0 | 0 | 0 |
|  | Anionic aqueous polyurethane dispersion - 3b | 0 | 30 | 0 | 0 | 0 | 0 |
| Phase B | Water | 5.5 | 22.5 | 27.9 | 22.6 | 45.2 | 44.2 |
|  | hydroxyethyl cellulose | 0 | 0 | 3 | 0.05 | 2 | 0 |
|  | xanthan gum | 0.1 | 0.5 | 0.5 | 1 | 1.5 | 1 |
|  | Carbomer | 0.1 | 0.2 | 3 | 0.0 | 1 | 1 |
|  | Gellan gum | 0.3 | 1 | 0 | 0 | 0 | 1.5 |
|  | Ceteareth-20 | 2 | 2 | 3 | 2 | 3 | 2.5 |
| Phase C | PEG-10 Polydimethylsiloxane | 3 | 1 | 3 | 2 | 2 | 4.5 |
|  | Coconut oil | 4 | 4 | 6 | 2 | 3 | 4 |
|  | Castor oil | 3 | 4 | 6 | 2 | 4 | 4 |
|  | Polydimethylsiloxane | 8 | 4 | 2 | 2 | 3 | 6 |
| Other components | Fragrance | 3 | 0.5 | 0.3 | 1 | 1 | 1 |
|  | Phenoxyethanol | 1 | 0.3 | 0.3 | 0.3 | 0.3 | 0.3 |
| Substrate type |  | Gel | Gel | Cream | Emulsion | Cream | Gel |

Comparative Examples 1-3

Comparative example 1: according to the components and their mass percentages shown in Table 2, at room temperature, the components of the phase B and the components of the phase C were mixed, stirred at 600 r/min for 5 min and then heated to 75° C. respectively, and the phase B and the phase C were mixed and homogenized at 8000 r/min for 5 min during which the temperature was maintained at 75° C. to obtain a phase B+C. After the temperature was reduced to 50° C., other components were added and homogenized at 5000 r/min for 5 min to prepare the mask substrate.

Comparative examples 2 and 3: according to the components and their mass percentages shown in Table 2, at room temperature, the components of the phase B and the components of the phase C were mixed, stirred at 600 r/min for 5 m and then heated to 75° C. respectively, and the phase B and the phase C were mixed and homogenized at 8000 r/min for 5 min during which the temperature was maintained at 75° C. to obtain a phase B+C. After the temperature dropped to 50° C., the phase A and other components were added and homogenized at 5000 r/min for 5 min to prepare the mask substrate.

TABLE 2

| | Components | Comparative example 1 | Comparative example 2 | Comparative example 3 |
|---|---|---|---|---|
| Phase A | Anionic aqueous polyurethane dispersion - 1a | 0 | 45 | 0 |
| | Anionic aqueous polyurethane dispersion - 2b | 0 | 0 | 45 |
| Phase B | Water | 72.9 | 27.9 | 27.9 |
| | Hydroxyethyl cellulose | 3 | 3 | 3 |
| | Xanthan gum | 0.5 | 0.5 | 0.5 |
| | Carbomer | 3 | 3 | 3 |
| Phase C | Ceteareth-20 | 3 | 3 | 3 |
| | PEG-10 polydimethylsiloxane | 3 | 3 | 3 |
| | Coconut oil | 6 | 6 | 6 |
| | Castor oil | 6 | 6 | 6 |
| | Polydimethylsiloxane | 2 | 2 | 2 |
| Other components | Fragrance | 0.3 | 0.3 | 0.3 |
| | Phenoxy ethanol | 0.3 | 0.3 | 0.3 |

Comparison Tests:

Mask preparation: at room temperature, hydrolyzed glycosaminoglycan whose mass was 1 wt % of the mask substrate was added to each of the mask substrates prepared in Example 10 and Comparative examples 1-3 (i.e., hydrolyzed glycosaminoglycan:mask substrate=1:100, by mass), and homogenized for 5 min to prepare masks, and in this way, masks with the mask substrates prepared in Example 10 and Comparative examples 1-3 as the substrates were prepared.

Efficacy evaluation of functional mask substrates: 17 subjects respectively used the above-obtained masks with the mask substrates prepared in Example 10 and Comparative examples 1-3 as the substrates, and uncovered the masks from their faces after 15 min.

Detection method: epidermal moisture content of the skin and the amount of wrinkle reduction were detected by using the transepidermal water loss tester (TEWL), epidermal moisture tester Corneometer and Visiacr used for wrinkle test.

Test Results:

For the skin conditions after the subjects used the mask with the mask substrate prepared in Example 10 as the substrate, compared with the skin conditions before the mask was used, the average amount of wrinkle reduction of the subjects was 18%, and the epidermal moisture content of the skin was increased by 61%, indicating that the prepared mask can significantly reduce transepidermal water loss and improve skin smoothness.

For the skin conditions after the subjects used the mask with the mask substrate prepared in Example 1 as the substrate, compared with the skin conditions before the mask was used, the amount of wrinkle reduction of the subjects was 18%, and the epidermal moisture content of the skin was increased by 49%. For the skin conditions after the subjects used the masks with the mask substrates prepared in Examples 2 and 3 as the substrates, compared with the skin conditions before the masks were used, the average amounts of wrinkle reduction of the subjects were 16.1% and 16.7 respectively, and the epidermal moisture contents of the skin were increased by 51% and 50.4% respectively.

The comparison test results confirmed that, compared with Comparative example 1, the aqueous polyurethane functional mask substrate prepared in Example 10 can increase the amount of wrinkle reduction by up to 12.5%, and moisturizing effect by up to 24.5%. It indicates that the mixed use of the anionic aqueous polyurethane dispersions a and b of the present disclosure has an apparent effect of promoting the deep conduction of active substances in the mask. Meanwhile, the results of Comparative examples 2 and 3 indicate that the use of the anionic aqueous polyurethane dispersions a or b alone has no apparent effect of promoting the deep conduction of active substances in the mask.

The mask substrates prepared in Examples 1-9 and 11-13 were subjected to the above comparison tests, and similar conclusions as in Example 10 were also obtained.

Meanwhile, the masks with mask substrates prepared in Examples 11, 12 and 13 as the substrates have better effects in terms of appearance, skin feel and consumer experience.

Furthermore, 10 subjects used the masks with the mask substrates prepared in Example 1-13 as the substrates. After about 15 min, the masks were completely dry. After the masks were moistened with water, all subjects could completely uncover the masks from the faces without pain.

What is claimed is:

1. A mask substrate composition, comprising, by total mass of the mask substrate composition, the following components: (a) 5-90 wt % of an aqueous polyurethane dispersion; and (b) 10-95 wt % of an aqueous polyurethane dispersion; wherein the aqueous polyurethane dispersion (a) is prepared by reaction of reaction raw materials comprising
- a1) polyisocyanate, (a2) polyester polyol, (a3) a low-molecular weight diol chain extender, (a4) a polyamine chain extender, (a5) a polyamine chain extender and (a6) a small-molecule monoamino end-capping agent; wherein the aqueous polyurethane dispersion (a) is prepared by reaction of the raw materials of the following mass percentages based on the mass of polyurethane:
- (a1) polyisocyanate 15-25 wt %;
- (a2) polyester polyol 65-80 wt %;
- (a3) a low-molecular weight diol chain extender 0.1-3 wt %;
- (a4) a polyamine chain extender (a) 0.01-3 wt %;
- (a5) a polyamine chain extender (b) 1-8 wt %; and
- (a6) a small-molecule monoamino end-capping agent 0.1-2 wt %;
- (b) the aqueous polyurethane dispersion (b) is prepared by reaction of reaction raw materials comprising (b1) polyisocyanate, (b2) polyester polyol, (b3) polyethylene glycol monomethyl ether, (b6) a polyhydroxyl chain extender, (b4) a polyamine chain extender and (b5) a polyamine chain extender; wherein the (b) aqueous polyurethane dispersion (b) is prepared by reaction of the raw materials of the following mass percentages based on the mass of polyurethane:
- (b1) polyisocyanate 14-35 wt %;
- (b2) polyester polyol 60-83.8 wt %;
- (b3) polyethylene glycol monomethyl ether 1-3 wt %;
- (b6) a polyhydroxyl chain extender 0.1-1 wt %;
- (b4) a polyamine chain extender 0.1-5 wt %; and
- (b5) a polyamine chain extender(b') 1-2 wt %; and wherein
- (a4) the polyamine chain extender and (b4) the polyamine chain extender are polyamine chain extenders which are not substituted by ionic or potentially ionic groups;
- (a5) the polyamine chain extender and (b5) the polyamine chain extender are polyamine chain extenders which are substituted by ionic or potentially ionic groups; and
- (b6) the polyhydroxy] chain extender is a low-molecular weight polyhydroxyl chain extender.

2. The mask substrate composition according to claim 1, wherein (a) the aqueous polyurethane dispersion (a) is prepared according to a method comprising the following steps: mixing (a2) the polyester polyol and (a3) the low-molecular weight diol chain extender at 70-80° C., lowering the temperature of the resulting mixture to 45-60° C., and then adding (a1) the polyisocyanate for a prepolymerization reaction; cooling the resulting prepolymer to 30-45° C. when the theoretical NCO content is reached, and dissolving the prepolymer in an acetone solvent in which the usage amount of acetone is 100-150 wt % of the mass of the polyurethane in (a) the aqueous polyurethane dispersion OA; after mixing the prepolymer and the acetone solvent, adding (a4) the polyamine chain extender (a) and (a5) the polyamine chain extender (b), continuing the reaction at 35-45° C. for 15-30 min, adding water under shear and dispersion conditions in which the usage amount of water is 130-200 wt % of the mass of the polyurethane in (a) the aqueous polyurethane dispersion (a), adding an aqueous solution of (a6) the small-molecule monoamino end-capping agent for end-capping, removing the acetone under vacuum, and obtaining (a) the aqueous polyurethane dispersion (a); and the total solids content of (a) the aqueous polyurethane dispersion (a) is 20-50 wt %; and the particle size is 100 nm-300 nm.

3. The mask substrate composition according to claim 1, wherein (b) the aqueous polyurethane dispersion (b) is prepared according to a method comprising the following steps: mixing (b1) the polyisocyanate, (b2) the polyester polyol, (b3) the polyethylene glycol monomethyl ether, (b6) the polyhydroxyl chain extender and acetone at 50-100° C., performing a prepolymerization reaction, and dissolving the resulting prepolymer in an acetone solvent when the theoretical NCO content is reached or approached, in which the overall usage amount of acetone in the preparation process is 100-210 wt % of the mass of the polyurethane in (b) the aqueous polyurethane dispersion (b); after mixing the prepolymer and the acetone solvent, adding (b4) the polyamine chain extender (a') and (b5) the polyamine chain extender (b'), continuing the reaction at 35-45° C. for 15-30 min, adding water under shear and dispersion conditions in which the usage amount of water is 100-170 wt % of the mass of the polyurethane in (b) the aqueous polyurethane dispersion (b), removing the acetone under vacuum, and obtaining (b) the aqueous polyurethane dispersion (b); and the total solids content of (b) the aqueous polyurethane dispersion (b) is 30-50 wt %, and the particle size is 120 nm-190 nm.

4. The mask substrate composition according to claim 1, wherein, (a1) the polyisocyanate has two isocyanate groups, and is one or more selected from the group consisting of aliphatic isocyanates and alicyclic isocyanates;
- (a2) the polyester polyol has a number-average molecular weight of 800-3000, and a functionality of 2-3; and (a2) the polyester polyol is prepared by a polymerization reaction of organic polycarboxylic acid and/or anhydride thereof and polyol, wherein the organic polycarboxylic acid and/or anhydride thereof are one or more selected from the group consisting of succinic acid, glutaric acid, adipic acid, pimelic acid, suberic acid, azelaic acid, sebacic acid, phthalic acid, isophthalic acid, terephthalic acid and anhydrides thereof; and the polyol is one or more selected from the group consisting of ethylene glycol, 1,2-propylene glycol, 1,4-butylene glycol, 1,3-butylene glycol, 1,6-hexylene glycol, trimethylolpropane and neopentyl glycol;
- (a3) the low-molecular weight diol chain extender is one or more selected from the group consisting of ethylene glycol, diethylene glycol, 1,3-propylene glycol, 1,2-propylene glycol, 1,4-butylene glycol, 1,3-butylene glycol, cyclohexanediol, 1,4-cyclohexanedimethanol, 1,6-hexylene glycol and neopentyl glycol;
- (a4) the polyamine chain extender (a) has 2-20 carbon atoms and a functionality of 2-3, and is one or more selected from the group consisting of ethylenediamine, propylene diamine, butanediamine, hexamethylenediamine, isophorone diamine, 1,4-cyclohexanediamine, 4,4'-dicyclohexylmethanediamine and diethylenetriamine;
- (a5) the polyamine chain extender (b) is diamine substituted by an ionic or potentially ionic group, and is a sodium salt of N-(2-aminoethyl)-2-aminoethanesulfonic acid and/or a sodium salt of N-(2-aminoethyl)-2-aminopropanesulfonic acid; and
- (a6) the small-molecule monoamino end-capping agent has 2-10 carbon atoms and a functionality of 1, and is diethanol amine, trihydroxy amine and/or 2-amino-2-methyl-1-propanol.

5. The mask substrate composition according to claim 4, wherein, (a1) the polyisocyanate is one or more selected from the group consisting of isophorone diisocyanate, 1,6-hexyl diisocyanate, dicyclohexylmethane diisocyanate and tetramethyl xylylene diisocyanate.

6. The mask substrate composition according to claim 1, wherein, (b1) the polyisocyanate has 2 to 4 isocyanate groups, and is one or more selected from the group consisting of aliphatic polyisocyanates and alicyclic polyisocyanates;
- (b2) the polyester polyol has a number-average molecular weight of 20-14000, and a functionality of 2-3; and (b2) the polyester polyol is prepared by a polymerization reaction of organic polycarboxylic acid and/or anhydride thereof and polyol, wherein the organic polycarboxylic acid and/or anhydride thereof are one or more selected from the group consisting of succinic acid, glutaric acid, adipic acid, pimelic acid, suberic acid, azelaic acid, sebacic acid, phthalic acid, isophthalic acid, terephthalic acid and anhydrides thereof; and the polyol is one or more selected from the group consisting of ethylene glycol, butanediol, neopentyl glycol and hexylene glycol;
- the number-average molecular weight of (b3) the polyethylene glycol monomethyl ether is 700-2000;
- (b4) the polyamine chain extender (a') has 2-13 carbon atoms and a functionality of 2-3, and is one or more selected from the group consisting of 1,2-ethylenediamine, 1,6-hexamethylenediamine, isophorone diamine, piperazine, 1,4-diaminocyclohexane, bis-(4-aminocyclohexyl)methane, N-(2-hydroxyethyl)ethylenediamine and diethylene triamine;
- (b5) the polyamine chain extender (b') is diamine substituted by an ionic or potentially ionic group, and is a sodium salt of N-(2-aminoethyl)-2-aminoethanesulfonic acid and/or a sodium salt of N-(2-aminoethyl)-2-aminopropanesulfonic acid; and
- (b6) the polyhydroxyl chain extender is trimethylolpropane.

7. The mask substrate composition according to claim 6, wherein, (b1) the polyisocyanate is one or more selected from the group consisting of hexamethylene diisocyanate, dodecamethylene diisocyanate, isophorone diisocyanate and 4,4'-dicyclohexylmethane diisocyanate.

8. A mask substrate, comprising the mask substrate composition according to claim 1, wherein, by the total mass of the mask substrate, the mass percentages of (a) the aqueous polyurethane dispersion (a) and (b) the aqueous polyurethane dispersion (b) in the mask substrate composition in the mask substrate are as follows:
- (a) 5-90 wt % of the aqueous polyurethane dispersion (a); and
- (b) 10-95 wt % of the aqueous polyurethane dispersion (b);
wherein the mask substrate further comprises components of the following mass percentages:
- (c) 0-10 wt % of a thickener;
- (d) 0-10 wt % of an emulsifier;
- (e) 0-20 wt % of a grease;
- (f) 0-1 wt % of a preservative;
- (g) 0-1 wt % of a fragrance; and
- (h) 0-80 wt % of deionized water.

9. The mask substrate according to claim 8, wherein the mask substrate is in an emulsion form, and by the total mass of the mask substrate, comprises the following components:
- (a) 20-70 wt % of the aqueous polyurethane dispersion (a);
- (b) 20-70 wt % of the aqueous polyurethane dispersion (b);
- (c) 0-15 wt % of a thickener;
- (d) 0-6 wt % of an emulsifier;
- (e) 0-10 wt % of a grease;
- (f) 0-1 wt % of a preservative;
- (g) 0-3 wt % of a fragrance; and
- (h) 0-60 wt % of deionized water.

10. The mask substrate according to claim 8, wherein the mask substrate is in a cream form, and by the total mass of the mask substrate, comprises the following components:
- (a) 10-50 wt % of the aqueous polyurethane dispersion (a);
- (b) 10-50 wt % of the aqueous polyurethane dispersion (b);
- (c) 0.2-10 wt % of a thickener;
- (d) 0-7 wt % of an emulsifier;
- (e) 0-15 wt % of a grease;
- (f) 0-1 wt % of a preservative;
- (g) 0-3 wt % of a fragrance; and
- (h) 0-79.8 wt % of deionized water.

11. The mask substrate according to claim 8, wherein the mask substrate is in a gel form, and by the total mass of the mask substrate, comprises the following components:
- (a) 10-60 wt % of the aqueous polyurethane dispersion (a);
- (b) 10-60 wt % of the aqueous polyurethane dispersion (b);
- (c) 0.5-10 wt % of a thickener;
- (d) 0-10 wt % of an emulsifier;
- (e) 0-20 wt % of a grease;
- (f) 0-1 wt % of a preservative;
- (g) 0-3 wt % of a fragrance; and
- (h) 0-71.5 wt % of deionized water.

12. The mask substrate according to any one of claim 8, wherein (c) the thickener is one or more selected from the group consisting of acrylic thickener, polyurethane thickener, cellulosic thickener, gellan gum, xanthan gum, carbomer, guar gum, diatomaceous earth, starch, arabic gum, soy protein gum, gelatin, sodium alginate, casein, chitosan, natural lanolin and agar;
- (d) the emulsifier is one or more selected from the group consisting of stearyl esters, polyether silicone oils, alkyl ethers, carboxylates, sulfates, sulfonates, amine derivatives, polyoxyethylene ethers and polyoxypropylene ethers;
- (e) the grease is one or more selected form the group consisting of natural oil, synthetic oil, mineral oil, fatty acid, fatty alcohol and fatty ester; and
- (f) the preservative is one or more selected from the group consisting of phenoxy ethanol, ethylhexylglycerin, caprylyl glycol and 1,2-hexylene glycol.

13. The mask substrate according to claim 9, wherein, by the total mass of the mask substrate, (c) the thickener is: 0-3.0 wt % of hydroxyethyl cellulose, 0-3.0 wt % of xanthan gum and 0-2.0 of wt % carbomer;
- (d) the emulsifier is 0-4.0 wt % of ceteareth-20 and 0-4.0 wt % of PEG-10 polydimethylsiloxane; and
- (e) the grease is 0-10 wt % of coconut oil, 0-10 wt % of castor oil and 0-10 wt % of polydimethylsiloxane.

14. The mask substrate according to claim 10, wherein, by the total mass of the mask substrate, (c) the thickener is: 0.1-5.0 wt % of hydroxyethyl cellulose, 0.1-5.0 wt % of xanthan gum and 0-5.0 wt % of carbomer;
- (d) the emulsifier is 0-4.0 wt % of ceteareth-20 and 0-5.0 wt % of PEG-10 polydimethylsiloxane; and (e) the grease is 2.0-10 wt % of coconut oil, 2.0-10 wt % of castor oil and 2.0-10 wt % of polydimethylsiloxane.

15. The mask substrate according to claim 11, wherein, by the total mass of the mask substrate, (c) the thickener is: 0.1-2.0 wt % of gellan gum, 0.1-6.0 wt % of xanthan gum and 0.1-5.0 wt % of carbomer;
   (d) the emulsifier is 0-4.0 wt % of ceteareth-20 and 0-4.5 wt % of PEG-10 polydimethylsiloxane; and
   (e) the grease is 0-10 wt % of coconut oil, 0-12 wt % of castor oil and 0-12 wt % of polydimethylsiloxane.

16. A method for preparing the mask substrate of claim 8, comprising the following steps:
   the aqueous polyurethane dispersion (a) and the aqueous polyurethane dispersion (b) are mixed to obtain a phase A; (h) the deionized water and (c) the thickener are mixed to obtain a phase B; and (d) the emulsifier and (e) the grease are mixed to obtain a phase C;
   in the presence of the phase C, the phase B and the phase C are respectively heated to 70-85° C. and mixed well to obtain a phase B+C, and after the temperature drops to the range of 50° C. to room temperature, the phase A and other components and are added and mixed well; and
   in the absence of the phase C, the phase A and the phase B are mixed at the room temperature to obtain a phase A+B, and other components are added and mixed well.

17. A facial mask or body mask, comprising the mask substrate composition according to claim 1 and an active substance.

18. A method for preparing the facial mask or body mask according to claim 16, comprising a step of mixing the mask substrate composition and the active substance.

\* \* \* \* \*